US009033498B2

(12) United States Patent
Naba

(10) Patent No.: US 9,033,498 B2
(45) Date of Patent: May 19, 2015

(54) PHOTOGRAPHING APPARATUS AND PHOTOGRAPHING METHOD

(71) Applicant: CANON KABUSHIKI KAISHA, Tokyo (JP)

(72) Inventor: Takashi Naba, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/734,058

(22) Filed: Jan. 4, 2013

(65) Prior Publication Data

US 2013/0182218 A1 Jul. 18, 2013

(30) Foreign Application Priority Data

Jan. 16, 2012 (JP) .................................. 2012-006009

(51) Int. Cl.
*A61B 3/14* (2006.01)
*G01B 9/02* (2006.01)
*A61B 3/10* (2006.01)

(52) U.S. Cl.
CPC ............ *G01B 9/02091* (2013.01); *A61B 3/102* (2013.01)

(58) Field of Classification Search
USPC ............................ 359/205, 206; 351/205, 206
See application file for complete search history.

(56) References Cited

U.S. PATENT DOCUMENTS

| 7,643,154 B2 | 1/2010 | Kikawa et al. |
| 2008/0151256 A1* | 6/2008 | Kikawa et al. ................ 356/496 |
| 2011/0181889 A1 | 7/2011 | Kabetani et al. |
| 2012/0013848 A1 | 1/2012 | Naba et al. |

FOREIGN PATENT DOCUMENTS

JP 2008-154939 A 7/2008

* cited by examiner

*Primary Examiner* — Mahidere Sahle
(74) *Attorney, Agent, or Firm* — Fitzpatrick, Cella, Harper & Scinto

(57) ABSTRACT

In order to place a coherence gate as close as possible to a object, provided is a tomographic image photographing apparatus including: a moving unit for moving the coherence gate corresponding to a difference between an optical path length of measuring light and an optical path length of reference light; and a control unit for controlling the moving unit so as to further move the coherence gate from a second position based on first combined light and second combined light of the object, which are respectively acquired at a first position of the coherence gate and the second position at which the coherence gate is placed after being moved from the first position to the object side by the moving unit.

32 Claims, 6 Drawing Sheets

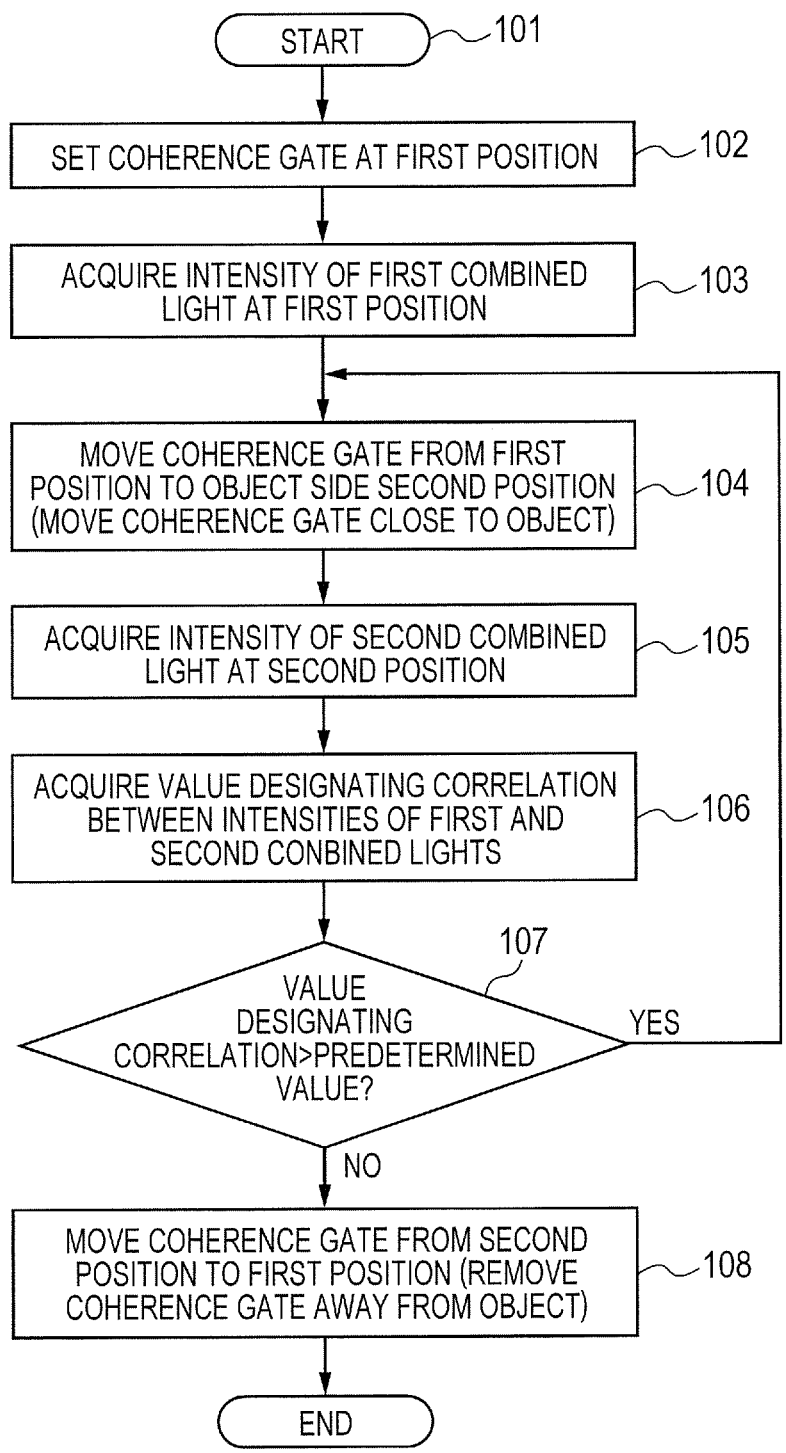

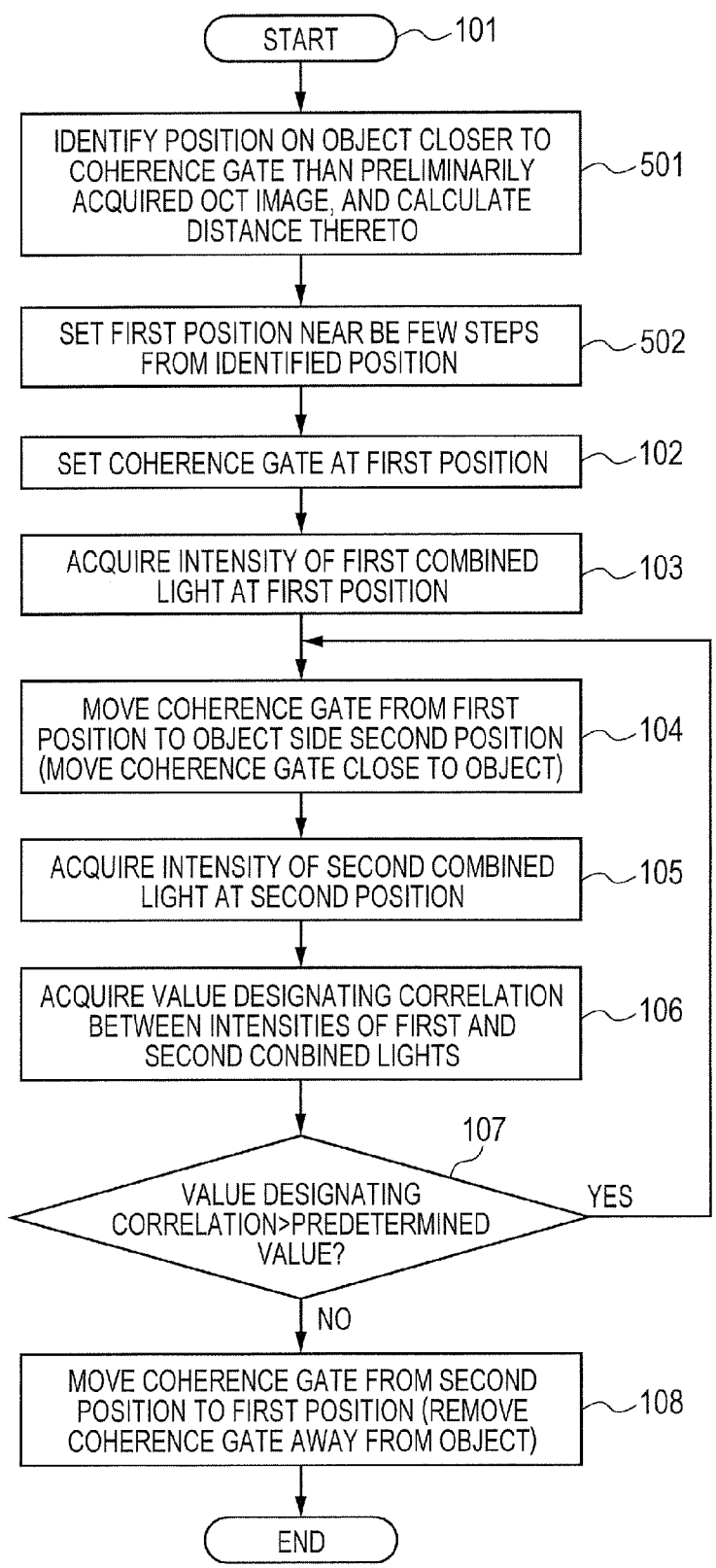

PHOTOGRAPHING APPARATUS AND PHOTOGRAPHING METHOD

BACKGROUND OF THE INVENTION

1. Field of the Invention

The present invention relates to a photographing apparatus for photographing a tomographic image through use of optical interference, and more particularly, to a photographing apparatus including an interference optical system used for ophthalmologic care and a photographing method.

2. Description of the Related Art

In recent years, as an ophthalmologic apparatus using an optical device, various apparatuses have been used. For example, as an optical device for observing an eye, various apparatus such as an anterior ocular segment photographing apparatus, a fundus camera, and a scanning laser ophthalmoscope (SLO) have been used. Of those, an optical coherence tomography (OCT) apparatus (hereinafter referred to as "OCT apparatus") is capable of acquiring a tomographic image of a sample with high resolution, and is becoming an apparatus necessary, as an ophthalmologic apparatus, for an out-patient clinic specializing in a retina.

The OCT apparatus irradiates a sample with low coherent light and disperses reflected light from the sample with an interference system to analyze and measure the sample with high sensitivity. Further, the OCT apparatus can acquire a tomographic image with high resolution by scanning the sample with the low coherent light. Therefore, the OCT apparatus can also photograph a tomographic image of a retina in a fundus of an eye to be inspected with high resolution, and hence, is being used widely in ophthalmologic diagnosis of a retina.

The OCT apparatus combines return light from an eye to be inspected, obtained by irradiating the eye to be inspected with low coherent light called measuring light through a scanning unit, with reference light corresponding to the measuring light, and acquires the above-mentioned tomographic image based on the obtained combined light. In this case, a position corresponding to an optical path length of the reference light in an optical path of the measuring light is referred to as a coherence gate. It is known that a tomographic image with higher resolution can be acquired as an object is closer to the coherence gate.

Japanese Patent Application Laid-Open No. 2008-154939 discloses a method of adjusting a signal-noise ratio of a one-dimensional sensor for analyzing combined light to a threshold value or more so as to adjust a coherence gate, for the purpose of acquiring a tomographic image of a retina with preferred resolution.

However, according to the method disclosed in Japanese Patent Application Laid-Open No. 2008-154939, a signal-noise ratio is used, and hence, it is difficult to determine an actual position of a coherence gate with respect to a retina. Therefore, in the case of acquiring a tomographic image with high resolution, there is a possibility that resolution at a position intended to be diagnosed may be degraded. Further, for example, in the case where cataract is developed in an eye to be inspected, and a signal-noise ratio cannot be obtained sufficiently, it is considered that it may be difficult to perform the above-mentioned control itself.

Further, in the conventional OCT apparatus, a tomographic image is photographed while being observed with a monitor. At this time, only a tomographic image which is being displayed is observed, and hence, it is difficult to perform an operation itself of bringing a coherence gate close to a retina.

SUMMARY OF THE INVENTION

The present invention has been made in view of the above-mentioned circumstances, and it is an object of the present invention to provide a photographing apparatus and method capable of setting a coherence gate as close as possible to an area to be photographed and acquiring a tomographic image with high resolution at a position intended to be diagnosed.

In order to solve the above-mentioned problems, according to an exemplary embodiment of the present invention, there is provided a photographing apparatus for photographing a tomographic image of a object based on combined light of return light from the object irradiated with measuring light and reference light corresponding to the measuring light, the photographing apparatus including: a moving unit for moving a coherence gate corresponding to a difference between an optical path length of the measuring light and an optical path length of the reference light; and a control unit for controlling the moving unit so as to move the coherence gate from a second position based on first combined light and second combined light of the object, which are respectively acquired at a first position of the coherence gate and the second position at which the coherence gate is placed after being moved from the first position to the object side by the moving unit.

Further, in order to solve the above-mentioned problems, according to another exemplary embodiment of the present invention, there is provided a photographing method of photographing a tomographic image of a object based on combined light of return light from the object irradiated with measuring light and reference light corresponding to the measuring light, the photographing method including: a moving step of moving a coherence gate corresponding to a difference between an optical path length of the measuring light and an optical path length of the reference light; and a step of moving the coherence gate from a second position based on first combined light and second combined light of the object, which are respectively acquired at a first position of the coherence gate and the second position at which the coherence gate is placed after being moved from the first position to the object side in the moving step.

According to the present invention, the coherence gate can be placed as close as possible to the object. This allows a tomographic image to be acquired with high resolution.

Further features of the present invention will become apparent from the following description of exemplary embodiments with reference to the attached drawings.

BRIEF DESCRIPTION OF THE DRAWINGS

FIG. 1 is a flowchart illustrating a first example according to the present invention.

FIG. 5 is a graph showing a relation between a position of a coherence gate and a correlation of continuous tomographic images.

FIG. 6 is a flowchart illustrating a second example according to the present invention.

DESCRIPTION OF THE EMBODIMENTS

First, an OCT apparatus used as a photographing apparatus according to an embodiment of the present invention is described. Note that, although a fundus (retina) of an eye to be inspected which is an exemplary object is described, the present invention is not limited thereto. For example, the object may be a skin, an organ, or the like of a subject. In this case, the present invention can be applied to medical equipment such as an endoscope, instead of an ophthalmologic apparatus.

Figure 2:
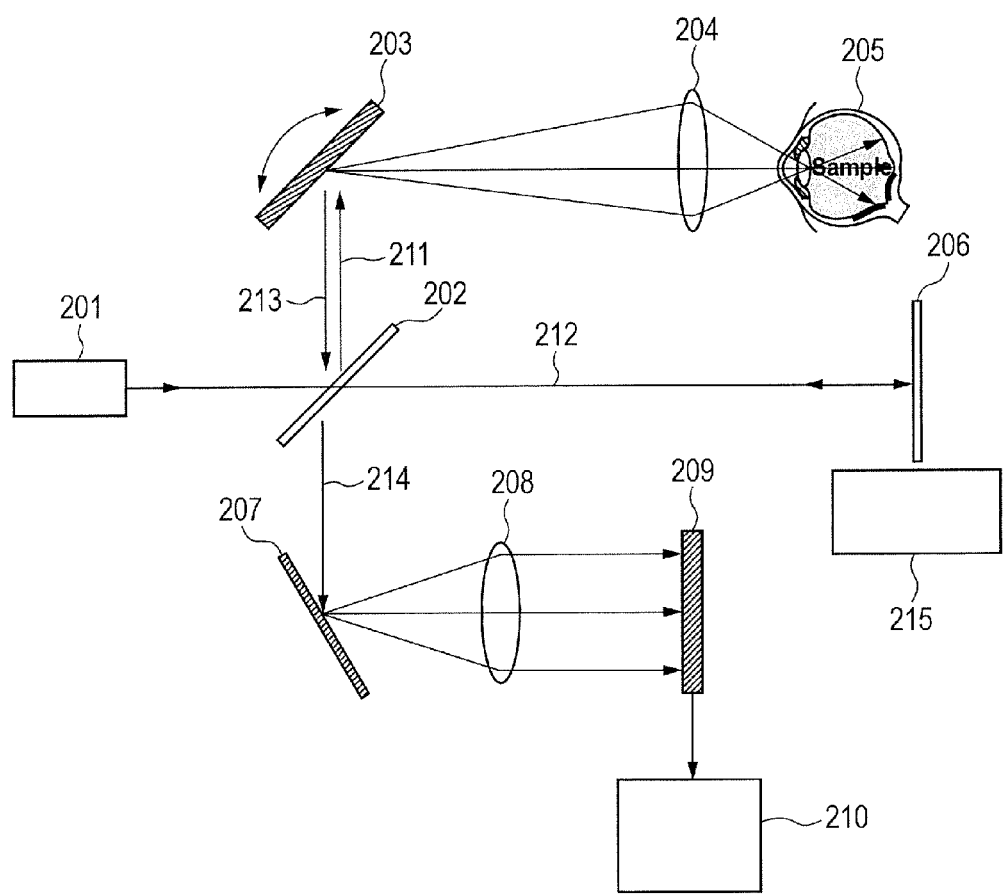
FIG. 2 is a diagram illustrating a schematic configuration of an SD-OCT apparatus according to an example of the present invention.

FIG. 2 is a conceptual diagram of a configuration of a spectral domain OCT (SD-OCT) apparatus which is a typical Fourier domain OCT (FD-OCT) apparatus. Light emitted from a light source 201 is split to reference light 212 and measuring light 211 by a beam splitter 202. The measuring light 211 is reflected or scattered by an eye 205 which is to be observed to return as return light 213, and thereafter, the measuring light 211 is combined with the reference light 212 by the beam splitter 202 to become interference light (combined light) 214. The interference light 214 is dispersed by a diffraction grating 207 and forms an image on a one-dimensional sensor 209 with a lens 208. Each output of the one-dimensional sensor 209 is subjected to Fourier transformation on a position in the one-dimensional sensor 209, that is, a frequency of the interference light, and thereby, a tomographic image of the eye 205 can be acquired in a control unit (CPU 210). The CPU 210 executes, through use of a corresponding module, each flow of the operations of moving a coherence gate by controlling a scanner, a mirror for reference light, and the like (described later) and obtaining a movement direction of the coherence gate.

Next, a periphery of the light source 201 is described. The light source 201 is a super luminescent diode (SLD) which is a typical low coherent light source. The light source 201 has a wavelength of 830 nm and a band width of 50 nm. In this case, the band width influences optical resolution in an optical axis direction of a tomographic image to be acquired, and hence, the band width is an important parameter. Further, although the SLD is selected as the light source in this case, any light source may be used as long as it can emit low coherent light, and an amplified spontaneous emission (ASE) or the like can also be used. Further, as for a wavelength, considering that the light is used for measuring an eye, infrared light is suitable. Further, the wavelength influences optical resolution in a lateral direction of a tomographic image to be acquired. Therefore, it is desired that the wavelength be as short as possible and the wavelength is set to 830 nm in this case. Depending on a measurement site of the object to be observed, it should be understood that other wavelengths may be selected.

Next, an optical path of the measuring light 211 is described. The measuring light 211 split by the beam splitter 202 enters a mirror of an XY scanner 203. In this case, for simplicity, the XY scanner 203 is described as one mirror. However, actually, two mirrors: a mirror for X scanning and a mirror for Y scanning are arranged closely to each other so as to perform raster scanning on a retina of the eye 205 in a direction perpendicular to an optical axis. Further, a center of the measuring light 211 is adjusted so as to be matched with a rotation center of the mirror of the XY scanner 203. The measuring light 211 is collected onto the retina by a lens 204. When the measuring light 211 enters the eye 205, the measuring light 211 is reflected or scattered from the retina of the eye 205 to become the return light 213 because of the above-mentioned optical system. In the present invention, the lens 204 and the like function as a focusing unit for moving in the optical axis direction by the CPU 210 to adjust a focus position of the measuring light 211. Further, the OCT apparatus includes a driving system for adjusting a position with respect to an eye to be inspected, and the driving system is included in the CPU 210 to function as a positioning unit for positioning an OCT apparatus which is a photographing apparatus with respect to the eye to be inspected.

Next, an optical path of the reference light 212 is described. The reference light 212 split by the beam splitter 202 is reflected by a mirror 206 to return to the beam splitter 202.

The mirror 206 can be moved in the optical axis direction by a driving device 215 to set an optical path length of the reference light 212 to be substantially the same as that of the measuring light 211, and thereby, the mirror 206 can cause the reference light 212 and the measuring light 211 to interfere with each other. The driving device can move the mirror 206 stepwise, generally with a stepping motor and the like.

Further, as described above, at a position of the eye to be observed, a position at which optical path length of the measuring light 211 becomes equal to the optical path length of the reference light 212 is called a coherence gate, and a tomographic image acquired in the apparatus is acquired as an image corresponding to a distance from the coherence gate. Next, a spectral system is described. As described above, the interference light 214 is dispersed by the diffraction grating 207, and the dispersion is performed under the same wavelength condition as the center wavelength and band width of the light source 201. Further, the one-dimensional sensor 209 for measuring interference light is generally classified into a CCD type and a CMOS type. However, the same effects can be obtained from either type.

Figure 3:
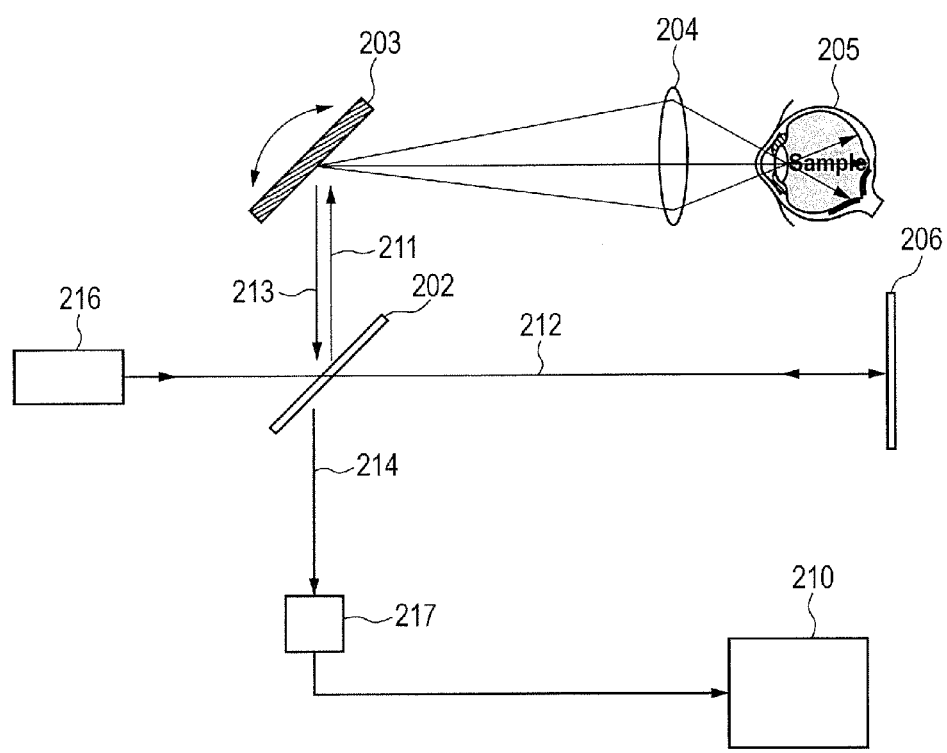
FIG. 3 is a diagram illustrating a schematic configuration of an SS-OCT apparatus according to the example of the present invention.

FIG. 3 is a conceptual diagram of a swept-source OCT (SS-OCT) apparatus which is another FD-OCT apparatus. The SS-OCT apparatus is different from the SD-OCT apparatus in that a light source is changed from low coherent light having a band width to a swept source 216 capable of scanning a wavelength of light, and a photoreceiver is changed from a spectroscope to a light-receiving element 217. That is, in the SD-OCT apparatus, a light source having a band width is dispersed in a light-receiving portion. However, in the SS-OCT apparatus, a wavelength of the light source is scanned and interference light is detected in synchronization with the scanning of the wavelength, and thereby, a signal can be obtained in the same way as in the one-dimensional sensor 209.

The swept source 216 of the SS-OCT apparatus can be realized by inserting a mirror resonator capable of changing a resonator length minutely into a ring-type fiber laser resonator. Further, the light-receiving element 217 can be realized by a PIN-type photodiode.

When measurement is performed without moving the XY scanner 203 in the above-mentioned OCT apparatus, a tomographic image of A-scan is acquired from an output of Fourier transformation. In this case, the A-scan refers to scanning in a depth direction (Z-direction) of the retina. When the XY scanner 203 continues to be moved by a resolution in an X-direction every time the A-scan is completed, a tomographic image of B-scan can be acquired. Further, by moving the XY scanner 203 in a Y-direction every time one tomographic image of the B-scan is acquired to acquire a continuous tomographic image of the B-scan, a three-dimensional tomographic image of the retina can be acquired.

As described above, the OCT apparatus has characteristics in which, as a coherence gate becomes closer to an object to be observed, a signal intensity becomes larger and a resolution becomes more satisfactory. Therefore, it is necessary to adjust the position of the mirror 206 so that a coherence gate is placed as close as possible to an object to be observed (retina in this case) in order to acquire an image with a higher signal-noise ratio and higher resolution.

Figures 1A, 4:
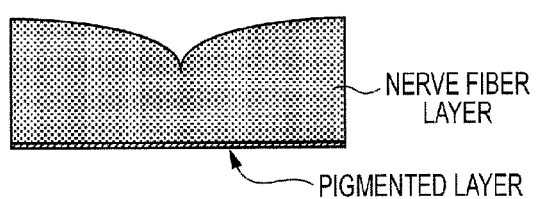
FIGS. 4-1A, 4-1B, 4-2A, 4-2B, 4-3A, 4-3B, 4-4A, 4-4B, 4-5A and 4-5B are diagrams illustrating relationships between an arrangement of a coherence gate and an actual tomographic image.
Figures 1B, 4:
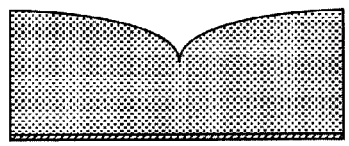
Figures 2A, 4:
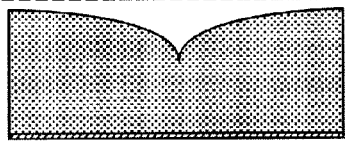
Figures 2B, 4:
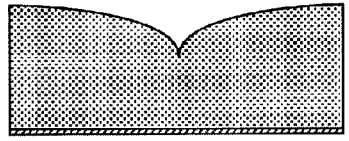
Figures 3A, 4:
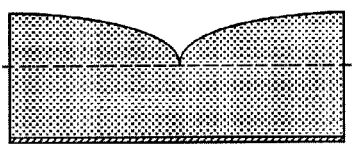
Figures 3B, 4:
Figures 4, 4A:
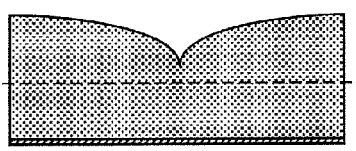
Figures 4, 4B:
Figures 4, 5, 5A:
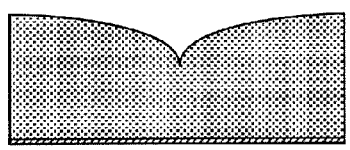
Figures 4, 5, 5B:
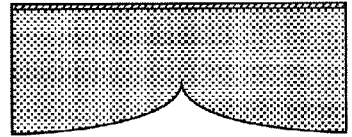
Figure 5:
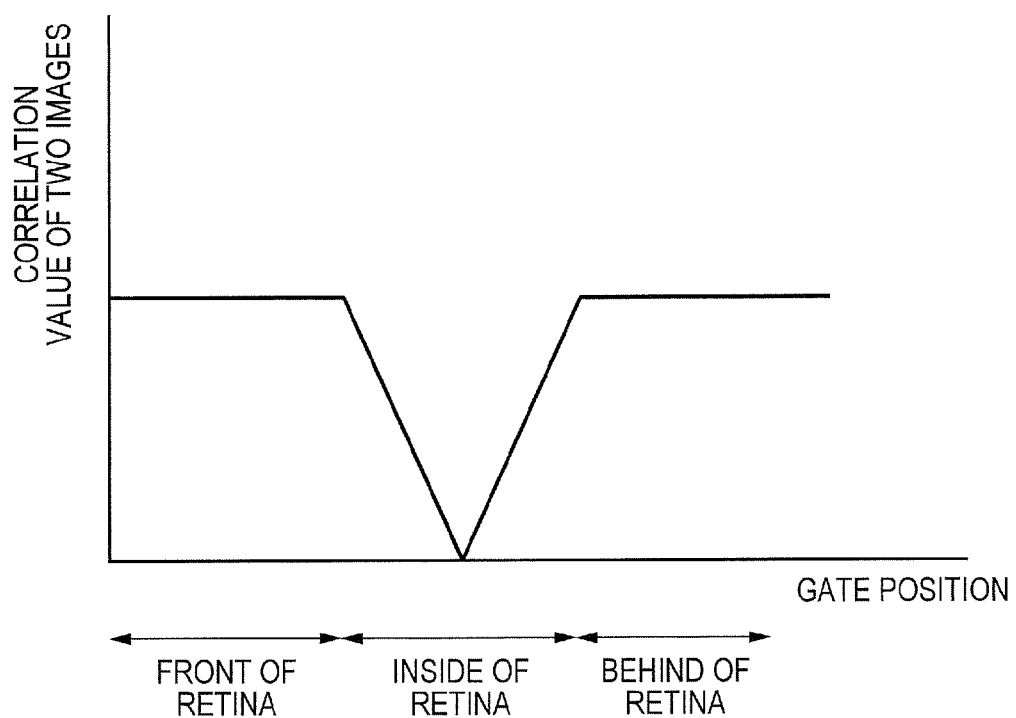

Specifically, as illustrated in FIGS. 4-1A to 4-5B, tomographic images which can be acquired when the coherence gate is brought close to an upper surface of the retina as in FIGS. 4-1A and 4-2A, images as in FIGS. 4-1B and 4-2B are acquired. However, in the case where the coherence gate enters the retina as in FIGS. 4-3A and 4-4A, tomographic images as in FIGS. 4-3B and 4-4B are acquired. Further, when the coherence gate passes through the retina as in FIG. 4-5A, an upside-down image as in FIG. 4-5B is acquired.

This is partly because only a distance from the coherence gate is known as the characteristics of the FD-type OCT apparatus. Thus, when the coherence gate is in the retina, a correct tomographic image cannot be acquired as described above, and hence, it is necessary to determine exactly whether the coherence gate is in or outside the retina.

According to the present invention, as described later, a tomographic image is acquired by bringing the coherence gate close to the retina from outside of the retina. When two tomographic images which can be acquired continuously in this case are compared with each other, in the case where the coherence gate is outside the retina, the shape of the tomographic image remains unchanged with only the position changed. However, as described with reference to FIGS. 4-3B and 4-4B, when the coherence gate is in the retina, the shape changes greatly. Based on this, when the correlation between the two tomographic images which can be acquired continuously is calculated, and this value changes, it can be determined that the coherence gate is in the retina.

FIG. 5 shows an exemplary value of a correlation in the retina. As shown in FIG. 5, when the coherence gate is outside the retina, images are the same, and hence, a correlation takes a large value. When the coherence gate is in the retina, a correlation decreases toward the center as shown in FIG. 5, and a correlation increases after passing through the center. When the coherence gate passes through the retina, an upside-down image is obtained as in FIG. 4-5B. At this time, a tomographic image does not change with respect to a change of the coherence gate, and hence, a correlation takes a large value. As described above, the coherence gate is brought close to the retina, and a position is found where a correlation between two tomographic images which can be acquired continuously changes. This position is determined to be a position where the coherence gate starts entering the retina, and the position of the coherence gate is adjusted to one step front of the retina.

Further, although a two-dimensional tomographic image is described for ease of understanding in FIGS. 4-1A to 4-5B, the same can be performed even with one A-scan.

First Example

FIG. 1 is a flowchart illustrating a control flow of the present invention for acquiring a three-dimensional image with high resolution, considering a relationship between the above-mentioned coherence gate and a tomographic image. The present invention is described with reference to FIG. 1. First, an operation is started in Step 101. When the flow is started, as an initialization operation, a coherence gate is set at an initial position away from a retina. An axial length of a human eye is generally about 20 mm to 30 mm, and hence, it is preferred that the coherence gate be set at a position of about 20 mm or less from a surface of the eye.

Next, the coherence gate is brought close to the retina step-by-step until an OCT image can be acquired. For acquiring an image of the retina, the B-scan is required in the case of monitoring the OCT image visually. However, in the case of performing monitoring automatically, the A-scan of one position is needed for the monitoring, because an interference signal only needs to be acquired. Further, in this case, Fourier transformation does not need to be performed. When the interference signal is acquired, a B-scan image of the OCT is acquired. A position of the retina closest to a current coherence gate position is identified from this image, and XY coordinates at that position are obtained and an XY scanner is fixed so that the position at the obtained coordinates is irradiated with measuring light.

After the above-mentioned operation is performed, in Step 102, the position of the coherence gate is set at a first position corresponding to the XY coordinates by moving the mirror 206 and the like. After the coherence gate is moved, an A-scan image is acquired to acquire an intensity of first combined light at the first position (Step 103). Then, in Step 104, the coherence gate is moved from the first position to a second position on an object side (coherence gate is brought close to the object). This movement can be grasped also as relatively rough first coherence gate adjustment performed based on the intensity of the combined light. Specifically, the coherence gate is brought close to the retina by one step. The coherence gate is moved to the second position, and thereafter, an A-scan image is acquired at that position in Step 105. Thus, an intensity of second combined light is acquired.

For moving the coherence gate, there are various methods of changing an optical path length, such as moving the mirror 206 and changing a distance between the OCT apparatus and the object as described above. In the present invention, these various methods are also included in a moving unit for moving the coherence gate. Specifically, the moving unit moves a coherence gate based on an optical path length difference which is a difference between an optical path length of measuring light and an optical path length of reference light.

In Step 106, a correlation between the A-scan image acquired in Step 105 and the A-scan image acquired in the previous step are calculated. Specifically, a value designating a correlation between intensities of first and second combined light beams is acquired. In Step 107, the value designating the correlation is compared with a predetermined value to determine whether a change of a predetermined value or more has occurred between the intensity of the first combined light and the intensity of the second combined light.

When the coherence gate is present in the retina as shown in FIG. 5, the intensity of the first combined light is also compared with the intensity of the second combined light during the operation of Step 107. For example, considering the case where the coherence gate is brought close to the retina by one step at a time from the front side of the retina, a value designating a correlation does not change greatly in a stage before the coherence gate reaches the retina. However, when the coherence gate enters the retina, the value designating the correlation decreases to become minimum at a center position of the retina. Then, the value increases until the coherence gate is positioned on a side behind the retina and becomes constant on the side behind the retina.

Thus, by knowing the tendency of a change in the value designating the correlation and the initial position of the coherence gate, it is possible to identify a direction in which the coherence gate is moved to be set to the intended position with respect to the retina. That is, the movement direction of the coherence gate can be acquired and determined based on the first combined light acquired at the first position and the second combined light acquired at the second position. In the present invention, the operation is performed by a module area which functions as a movement direction acquiring unit for acquiring the movement direction of the coherence gate in the CPU 210. Further, the control of the moving unit for moving the coherence gate from the second position is performed by a module area which functions as a control unit. By acquiring the movement direction appropriately, even after the coherence gate has been moved to some degree or more, an appropriate direction for moving the coherence gate to a preferred position can be obtained appropriately.

Returning to the flow, when the value designating the correlation is larger than the predetermined value in Step 107, the flow returns to Step 104, and the coherence gate is moved to a position closer to the object side from the second position. That is, in the case where the value designating the correlation is larger than the predetermined value, it is necessary to move the coherence gate from the second position to a third position on the object side, and hence, the movement direction acquiring unit acquires this movement direction. Further, in Step 107, an operation for acquiring again the movement direction of the coherence gate based on the correlation between the intensities of the second combined light and third combined light of the object acquired at the third position is performed. Then, the operation is repeated until the value designating the correlation reaches a predetermined value or less in Step 107.

When it is determined that the value designating the correlation is equal to or smaller than the predetermined value in Step 107, the flow proceeds to Step 108. In Step 108, it is considered that the current position of the coherence gate is one step beyond an optimum position, and the position of the coherence gate at the previous step is determined to be an optimum position. Acquiring the optimum position and adjusting the coherence gate as a result of the acquisition of the optimum position can be grasped as second coherence gate adjustment to be performed based on the correlation, which is relatively fine or finer than the first coherence gate adjustment.

In the present invention, a unit for forming a tomographic image or acquiring a tomographic image corresponds to a module area for forming a tomographic image or a three-dimensional image with combined light in the CPU 210. The tomographic image acquiring unit performs formation of a three-dimensional image and the like with combined light in a state in which the coherence gate is present at the position at the previous step. That is, the tomographic image acquiring unit acquires a tomographic image of an object in response to the completion of the movement of the coherence gate by the moving unit. It is preferred that the CPU 210 be provided with a monitor which is a display unit, and further, be provided with a display control unit for displaying the completion of adjustment of the coherence gate on the monitor with character display or the like. Further, it is preferred that the coherence gate be moved by the moving unit in the CPU 210 after the completion of adjustment of a focus position by a focusing unit and positioning by a positioning unit.

Here, the above-mentioned moving unit of the coherence gate moves the coherence gate in a movement direction acquired by the movement direction acquiring unit. The operation of the moving unit is performed by a module area which functions as a control unit for controlling the moving unit so as to move the coherence gate from the second position in the movement direction acquired by the movement direction acquiring unit in the CPU 210.

As a method of calculating the above-mentioned correlation, for example, there is a method of obtaining an inverse number of a root mean square of a difference in intensities of luminance of two images or the like. According to the method, when the intensities of two images are respectively represented by A(x) and B(x), a correlation to be obtained is expressed by an inverse number of a square root of a value obtained by dividing a total of squares of the differences A(x)−B(x) of the intensities of the respective points by the number of x points (data number). Further, generally, one coordinate is changed and a largest correlation is taken. In this case, it is known that a reflected light amount of a pigmented layer is largest, and hence, calculation can be performed quickly by taking a correlation based on a coordinate at which the intensity is largest.

In this example, when there is a change point of a calculated value of a correlation, it is immediately determined that the coherence gate is in the retina. However, in the case where noise and the like are large, even when there is a change point, operations in Steps 105 and 106 are performed multiple times to check an increase in the calculated value, and thereby, determination with higher accuracy can be made.

Further, in this example, Step 104 is directed to the B-scan image which is a two-dimensional tomographic image. However, in the case of acquiring a three-dimensional tomographic image, a tomographic image to be acquired can be set to be three-dimensional. Accordingly, a position of the retina closest to the current coherence gate position in the three-dimensional image can be found.

Further, in the above-mentioned example, a movement direction of the coherence gate is determined from the correlation of intensities. However, the movement direction can also be determined from similarity of images, for example. That is, the movement direction acquiring unit may be configured to acquire a movement direction of the coherence gate based on similarity of the first and second tomographic images acquired by the tomographic image acquiring unit.

A configuration may have a first photographing mode of setting a coherence gate outside an object in advance and photographing a tomographic image and a second photographing mode of setting the coherence gate in the object in advance and photographing a tomographic image. As described above, in photographing of a tomographic image, an image with a most preferred resolution is acquired at a position where the coherence gate is present and in the vicinity thereof. For example, in the case where an object is a human eye, there is a case where a nerve fiber layer on the surface side of the retina is desired to be analyzed in detail, and a case where a pigmented layer at the back of the retina is desired to be analyzed in detail. In the case where the nerve fiber layer is targeted, a three-dimensional image of the nerve fiber layer with high resolution can be acquired even in a short period of time by moving the coherence gate from the front side of the retina as in the above-mentioned example.

However, in the case where the pigmented layer is targeted, when measurement is started from the front side of the retina, it takes considerable time for measurement. In this case, by setting the coherence gate in the retina in advance and moving the coherence gate toward the back of the retina from the current position in the above-mentioned second photographing mode, a three-dimensional image of the pigmented layer with high resolution can be acquired in a short period of time. Further, regarding the nerve fiber layer, there may be a case where information on the surface side in the thickness direction is important and a case where information at the back thereof is important. By selecting these modes appropriately, an image at a desired position can be acquired with higher resolution in a short period of time.

In the present invention, the mode selection is performed by a selecting unit for selecting the first photographing mode of photographing a tomographic image of an object with a coherence gate being outside the object and a second photographing mode of acquiring a tomographic image of an object with the coherence gate being in the object. Note that, the selecting unit may be designed in such a manner that an operator can select a photographing mode through use of a switch, or a photographing mode can be selected through the CPU 210, and the movement direction acquiring unit may acquire a movement direction of a coherence gate automatically based on a value designating the correlation between two combined light beams.

In the case of a configuration with the selecting unit added thereto, it is required for the movement direction acquiring unit to acquire a movement direction of a coherence gate based on two combined light beams and an instruction from the selecting unit.

Specifically, the movement direction acquiring unit acquires a movement direction in which the coherence gate is moved from the second position to the first position side in a case where the selecting unit selects the first photographing mode and a value designating the correlation is smaller than a predetermined value.

Further, the movement direction acquiring unit acquires a movement direction in which the coherence gate is moved from the second position to the third position on the object side in a case where the selecting unit selects the second photographing mode and the value designating the correlation is smaller than the predetermined value, and acquires a movement direction of the coherence gate again based on a correlation between intensities of the second combined light and third combined light of the object acquired at the third position. In this case, unlike the case of searching for a preferred position of the coherence gate from the outside of the object, it is determined that the coherence gate is present at a preferred position in the object at the third position in the case where a correlation is larger than a predetermined value. Thus, a tomographic image of the object is acquired based on third combined light obtained at the third position of the coherence gate.

Second Embodiment

FIG. 6 is a flowchart illustrating a control flow of the second embodiment. In the first embodiment, a position closest to the current coherence gate position is obtained in Step 102 and the coherence gate is moved to the obtained position as a first position, and thereafter, the subsequent flow following the acquisition of the intensity of combined light is performed.

In the second embodiment, a distance between the obtained position and the coherence gate is calculated from an OCT tomographic image acquired when the first position is obtained, and the coherence gate is moved to the front of the first position through use of the distance, and thereafter, the same process as that of the first embodiment is performed.

Specifically, in Step 501, the distance between the position closest to the current coherence gate position and the coherence gate is calculated. Next, in Step 502, the coherence gate is moved to a position few steps from the above-mentioned closest position through use of the distance obtained in Step 501. The processes before and after these operations are the same as those in the first embodiment.

Accordingly, the coherence gate can be moved to an intended position rapidly, and processing can be performed rapidly.

As described above, one embodiment of the present invention is an embodiment of a Fourier domain OCT tomographic photographing apparatus. In the one embodiment, for adjusting the position of a coherence gate, a tomographic image is acquired while bringing the coherence gate close to a retina from the outside of the retina, and a correlation between two tomographic images acquired continuously is calculated. A position of the coherence gate before a value of the correlation changes is set to a first position of an adjustment position to be the reference. In this case, it is preferred that the coherence gate be brought close to the retina at a certain interval. Further, from the viewpoint of reduction in measurement time and alleviation of a load on the CPU, it is preferred to use A-scan tomographic images as the tomographic images of which the correlation is calculated. In this case, according to the method of calculating the correlation of the present invention, an inverse number of a root mean square of data at respective coordinates of two tomographic images is used. Further, when a tomographic image is acquired while bringing the coherence gate close to the retina, it is preferred that the position closest to the coherence gate be detected from a tomographic image acquired first, an A-scan tomographic image of the position be acquired, and a correlation be calculated. Further, in this case, after the position closest to the coherence gate is detected, the coherence gate may be moved to the vicinity in front of the position where the coherence gate is detected, and the coherence gate may be brought close to the retina at a certain interval therefrom.

Another Embodiment

Further, the present invention is realized also by performing the following processes. That is, software (program) for realizing the functions of the above-mentioned embodiments is supplied to a system or an apparatus via a network or various storage media, and a computer (CPU, MPU, or the like) of the system or the apparatus reads and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-006009, filed Jan. 16, 2012, which is hereby incorporated by reference herein in its entirety.

What is claimed is:

1. A photographing apparatus for photographing a tomographic image of an object based on combined light of return light from the object irradiated with measuring light and reference light corresponding to the measuring light, the photographing apparatus comprising:

a moving unit configured to move a coherence gate corresponding to a difference between an optical path length of the measuring light and an optical path length of the reference light;

a moving direction acquiring unit configured to acquire a moving direction of the coherence gate based on first combined light and second combined light, which are respectively acquired at a first position of the coherence gate and a second position at which the coherence gate is placed after being moved from the first position toward the object by the moving unit; and a control unit configured to control the moving unit so as to move the coherence gate in the acquired movement direction from the second position.

2. A photographing apparatus according to claim 1, further comprising a tomographic image acquiring unit configured to acquire a first tomographic image and a second tomographic image of the object respectively based on the first combined light and the second combined light, wherein the movement direction acquiring unit acquires the movement direction of the coherence gate based on the similarity between the first tomographic image and the second tomographic image.

3. A photographing apparatus according to claim 1, wherein the movement direction acquiring unit acquires the movement direction of the coherence gate based on a correlation between intensities of the first combined light and the second combined light.

4. A photographing apparatus according to claim 3, wherein the movement direction acquiring unit acquires a movement direction in which the coherence gate is moved from the second position to the first position side in a case where a value designating the correlation is smaller than a predetermined value.

5. A photographing apparatus according to claim 1, further comprising a tomographic image acquiring unit configured to acquire a tomographic image of the object based on the second combined light in response to completion of movement of the coherence gate from the second position toward the first position by the moving unit.

6. A photographing apparatus according to claim 3, wherein the movement direction acquiring unit acquires a movement direction in which the coherence gate is moved from the second position to a third position closer to the object than the second position in a case where a value designating the correlation is larger than a predetermined value, and acquires a movement direction of the coherence gate based on a correlation between intensities of the second combined light and third combined light of the object, which is acquired at the third position.

7. A photographing apparatus according to claim 1, further comprising a selecting unit configured to select a first photographing mode of photographing a tomographic image of the object with the coherence gate being outside the object and a second photographing mode of photographing a tomographic image of the object with the coherence gate being inside the object, wherein the movement direction acquiring unit acquires the movement direction of the coherence gate based on a result of the selection by the selecting unit and a correlation between intensities of the first combined light and the second combined light.

8. A photographing apparatus according to claim 7, wherein the movement direction acquiring unit acquires a movement direction in which the coherence gate is moved from the second position toward the first position in a case where the selecting unit selects the first photographing mode and a value designating the correlation is smaller than a predetermined value.

9. A photographing apparatus according to claim 7, wherein the movement direction acquiring unit acquires a movement direction in which the coherence gate is moved from the second position to a third position closer to the object than the second position in a case where the selecting unit selects the second photographing mode and a value designating the correlation is smaller than a predetermined value, and acquires the movement direction of the coherence gate based on a correlation between intensities of the second combined light and third combined light of the object, which is acquired at the third position.

10. A photographing apparatus according to claim 9, further comprising a tomographic image acquiring unit for acquiring a tomographic image of the object based on the third combined light at the third position of the coherence gate by the moving unit in a case where the value designating the correlation is larger than the predetermined value.

11. A photographing apparatus according to claim 1, wherein the control unit further comprises a display control unit configured to control a display unit to display completion of adjustment of the coherence gate by the moving unit.

12. A photographing apparatus according to claim 1, further comprising:
a focusing unit configured to adjust a focus position of the measuring light; and
a positioning unit configured to position the object and the photographing apparatus,
wherein the coherence gate is moved by the moving unit under a control of the control unit after completion of the adjustment of the focus position by the focusing unit and the positioning by the positioning unit.

13. A photographing apparatus according to claim 1, wherein the object is an eye to be inspected, which is a human eye.

14. A photographing apparatus according to claim 3, wherein the control unit controls the moving unit to perform a first coherence gate adjustment based on an intensity of the combined light and then controls the moving unit to perform a second coherence gate adjustment based on a correlation between the intensities.

15. A photographing method of photographing a tomographic image of an object based on combined light of return light from the object irradiated with measuring light and reference light corresponding to the measuring light, the photographing method comprising:
moving a coherence gate corresponding to a difference between an optical path length of the measuring light and an optical path length of the reference light;
acquiring a movement direction of the coherence gate based on the first combined light and the second combined light which are respectively acquired at a first position of the coherence gate and a second position at which the coherence gate is placed after being moved from the first position toward the object; and
moving the coherence gate in the acquired movement direction from the second position.

16. A photographing method according to claim 15, wherein, in acquiring the movement direction, a first tomographic image and a second tomographic image of the object are acquired respectively based on the first combined light and the second combined light, and the movement direction of the coherence gate is acquired based on similarity between the first tomographic image and the second tomographic image.

17. A non-transitory computer-readable storage medium storing a program causing a computer to perform the steps of the photographing method according to claim 15.

18. A photographing method according to claim 15, wherein, in acquiring the movement direction, the movement direction of the coherence gate is acquired based on a correlation between intensities of the first combined light and the second combined light.

19. A photographing apparatus for photographing a tomographic image of an object based on combined light of return light from the object irradiated with measuring light and reference light corresponding to the measuring light, the photographing apparatus comprising:
- a moving unit configured to move a coherence gate corresponding to a difference between an optical path length of the measuring light and an optical path length of the reference light;
- a tomographic image acquiring unit configured to acquire a first tomographic image and a second tomographic image of the object respectively based on first combined light and second combined light, which are respectively acquired at a first position of the coherence gate and a second position of the coherence gate; and
- a control unit configured to control the moving unit based on comparing the acquired first tomographic image with the acquired second tomographic image.

20. A photographing apparatus according to claim 19, wherein the control unit controls the moving unit based on comparing intensity of the acquired first tomographic image with intensity of the acquired second tomographic image.

21. A photographing apparatus according to claim 19, wherein the control unit controls the moving unit based on similarity between the acquired first tomographic image and the acquired second tomographic image.

22. A photographing apparatus according to claim 19, wherein the control unit controls the moving unit based on a correlation between the acquired first tomographic image and the acquired second tomographic image.

23. A photographing apparatus for photographing a tomographic image of an object based on combined light of return light from the object irradiated with measuring light and reference light corresponding to the measuring light, the photographing apparatus comprising:
- a moving unit configured to move a coherence gate corresponding to a difference between an optical path length of the measuring light and an optical path length of the reference light; and
- a control unit configured to control the moving unit based on comparing intensity of first combined light with intensity of second combined light, which are respectively acquired at a first position of the coherence gate and a second position of the coherence gate.

24. A photographing apparatus according to claim 23, wherein the control unit controls the moving unit based on a correlation between intensities of the first combined light and the second combined light.

25. A photographing method of photographing a tomographic image of an object based on combined light of return light from the object irradiated with measuring light and reference light corresponding to the measuring light, the photographing method comprising:
- moving, by a moving unit, a coherence gate corresponding to a difference between an optical path length of the measuring light and an optical path length of the reference light;
- acquiring a first tomographic image and a second tomographic image of the object respectively based on first combined light and second combined light, which are respectively acquired at a first position of the coherence gate and a second position of the coherence gate; and
- controlling the moving unit based on comparing the acquired first tomographic image with the acquired second tomographic image.

26. A photographing method according to claim 25, wherein, in controlling the moving unit, the moving unit is controlled based on comparing intensity of the acquired first tomographic image with intensity of the acquired second tomographic image.

27. A photographing method according to claim 25, wherein, in controlling the moving unit, the moving unit is controlled based on similarity between the acquired first tomographic image and the acquired second tomographic image.

28. A photographing method according to claim 25, wherein, in controlling the moving unit, the moving unit is controlled based on a correlation between the acquired first tomographic image and the acquired second tomographic image.

29. A photographing method for photographing a tomographic image of an object based on combined light of return light from the object irradiated with measuring light and reference light corresponding to the measuring light, the photographing method comprising:
- moving, by a moving unit, a coherence gate corresponding to a difference between an optical path length of the measuring light and an optical path length of the reference light; and
- controlling the moving unit based on comparing intensity of first combined light with intensity of second combined light, which are respectively acquired at a first position of the coherence gate and a second position of the coherence gate.

30. A photographing method according to claim 29, wherein, in controlling the moving unit, the moving unit is controlled based on a correlation between intensities of the first combined light and the second combined light.

31. A non-transitory computer-readable storage medium storing a program causing a computer to perform the steps of the photographing method according to claim 25.

32. A non-transitory computer-readable storage medium storing a program causing a computer to perform the steps of the photographing method according to claim 29.

* * * * *